(12) United States Patent
Calhoun et al.

(10) Patent No.: US 10,255,997 B2
(45) Date of Patent: Apr. 9, 2019

(54) MEDICAL ANALYTICS SYSTEM

(71) Applicant: Mindshare Medical, Inc., Seattle, WA (US)

(72) Inventors: Michael E. Calhoun, Seattle, WA (US); Samir Chowdhury, La Jolla, CA (US); Ilya Goldberg, Seattle, WA (US)

(73) Assignee: Mindshare Medical, Inc., Seattle, WA (US)

( * ) Notice: Subject to any disclaimer, the term of this patent is extended or adjusted under 35 U.S.C. 154(b) by 0 days.

(21) Appl. No.: 16/140,374

(22) Filed: Sep. 24, 2018

(65) Prior Publication Data

US 2019/0027252 A1 Jan. 24, 2019

Related U.S. Application Data

(63) Continuation of application No. 16/077,994, filed as application No. PCT/US2017/041735 on Jul. 12, 2017.

(Continued)

(51) Int. Cl.
*G16H 50/20* (2018.01)
*G06T 7/168* (2017.01)
(Continued)

(52) U.S. Cl.
CPC ............ *G16H 50/20* (2018.01); *A61B 6/488* (2013.01); *G06T 7/0012* (2013.01); *G06T 7/168* (2017.01);
(Continued)

(58) Field of Classification Search
CPC ........ G06T 7/168; G06T 7/0012; A61B 6/488
See application file for complete search history.

(56) References Cited

U.S. PATENT DOCUMENTS 4,907,156 A   3/1990  Doi et al.
5,133,020 A   7/1992  Giger et al.
(Continued)

FOREIGN PATENT DOCUMENTS

WO    WO-96/00425 A2    1/1996
WO    WO-2008/035286 A2    3/2008
(Continued)

OTHER PUBLICATIONS

Depeursinge, A., et al. (2007) "Image-based diagnostic aid for interstitial lung disease with secondary data integration." Proc. of SPIE, vol. 6514, 12 pages.
(Continued)

*Primary Examiner* — Edward Park
(74) *Attorney, Agent, or Firm* — Mintz Levin Cohn Ferris Glovsky and Popeo, P.C.

(57) ABSTRACT

Systems and methods of a medical analytics system are described herein. The medical analytics system can include a machine learning model for processing patient tissue images for either training the machine learning model or for clinical use, such as providing information for assisting a clinician with at least diagnosing a disease or condition of a patient. Implementations of the medical analytics system can further include a user interface that is configured to allow a user to interact with a patient image for assisting with diagnosing at least a part of the tissue captured in the patient image.

18 Claims, 7 Drawing Sheets

Related U.S. Application Data (60) Provisional application No. 62/361,421, filed on Jul. 12, 2016.

(51) Int. Cl.

| | |
|---|---|
| *G06T 7/00* | (2017.01) |
| *A61B 6/00* | (2006.01) |
| *G16H 80/00* | (2018.01) |
| *G06K 9/52* | (2006.01) |
| *G16H 50/30* | (2018.01) |
| *G16H 30/00* | (2018.01) |

(52) U.S. Cl.
CPC ............ *G06K 9/522* (2013.01); *G16H 30/00* (2018.01); *G16H 50/30* (2018.01); *G16H 80/00* (2018.01)

(56) References Cited

U.S. PATENT DOCUMENTS

| | | | |
|---|---|---|---|
| 5,289,374 | A | 2/1994 | Doi et al. |
| 5,452,367 | A | 9/1995 | Bick et al. |
| 5,537,485 | A | 7/1996 | Nishikawa et al. |
| 5,638,458 | A | 6/1997 | Giger et al. |
| 5,657,362 | A | 8/1997 | Giger et al. |
| 5,832,103 | A | 11/1998 | Giger et al. |
| 5,881,124 | A | 3/1999 | Giger et al. |
| 5,931,780 | A | 8/1999 | Giger et al. |
| 5,974,165 | A | 10/1999 | Giger et al. |
| 5,984,870 | A | 11/1999 | Giger et al. |
| 6,032,678 | A | 3/2000 | Rottem |
| 6,112,112 | A | 8/2000 | Gilhuijs et al. |
| 6,138,045 | A | 10/2000 | Kupinski et al. |
| 6,185,320 | B1 | 2/2001 | Bick et al. |
| 6,205,348 | B1 | 3/2001 | Giger et al. |
| 6,280,387 | B1 | 8/2001 | Deforge et al. |
| 6,282,305 | B1 | 8/2001 | Huo et al. |
| 6,282,307 | B1 | 8/2001 | Armato, III et al. |
| 6,317,617 | B1 | 11/2001 | Gilhuijs et al. |
| 6,335,980 | B1 | 1/2002 | Armato, III et al. |
| 6,442,287 | B1 | 8/2002 | Jiang et al. |
| 6,483,934 | B2 | 11/2002 | Armato, III et al. |
| 6,724,925 | B2 | 4/2004 | Armato, III et al. |
| 6,755,787 | B2 | 6/2004 | Hossack et al. |
| 6,855,114 | B2 | 2/2005 | Drukker et al. |
| 6,898,303 | B2 | 5/2005 | Armato, III et al. |
| 6,901,156 | B2 | 5/2005 | Giger et al. |
| 7,123,762 | B2 | 10/2006 | Giger et al. |
| 7,184,582 | B2 | 2/2007 | Giger et al. |
| 7,244,230 | B2 | 7/2007 | Duggirala et al. |
| 7,298,881 | B2 | 11/2007 | Giger et al. |
| 7,298,883 | B2 | 11/2007 | Giger et al. |
| 7,418,123 | B2 | 8/2008 | Giger et al. |
| 7,444,011 | B2 | 10/2008 | Pan et al. |
| 7,596,401 | B2 | 9/2009 | Yankelevitz et al. |
| 7,761,240 | B2 | 7/2010 | Saidi et al. |
| 7,769,215 | B2 | 8/2010 | Horsch et al. |
| 7,783,094 | B2 | 8/2010 | Collins et al. |
| 7,848,558 | B2 | 12/2010 | Giger et al. |
| 7,983,732 | B2 | 7/2011 | Chen et al. |
| 8,121,245 | B2 | 2/2012 | Pan et al. |
| 8,396,266 | B2 | 3/2013 | Kadir et al. |
| 8,423,118 | B2 | 4/2013 | Wenzel et al. |
| 8,650,005 | B2 | 2/2014 | Liao |
| 8,705,819 | B2 | 4/2014 | Carlsen et al. |
| 8,711,149 | B2 | 4/2014 | Schmidt et al. |
| 9,025,843 | B2 | 5/2015 | Pan et al. |
| 9,208,556 | B2 | 12/2015 | Giger et al. |
| 9,536,305 | B2 | 1/2017 | Giger et al. |
| 2001/0021264 | A1 | 9/2001 | Armato et al. |
| 2001/0043729 | A1 | 11/2001 | Giger et al. |
| 2002/0006216 | A1 | 1/2002 | Armato et al. |
| 2002/0009215 | A1 | 1/2002 | Armato et al. |
| 2002/0025063 | A1 | 2/2002 | Jiang et al. |
| 2002/0196966 | A1 | 12/2002 | Jiang et al. |
| 2003/0053674 | A1 | 3/2003 | Armato et al. |
| 2003/0125621 | A1 | 7/2003 | Drukker et al. |
| 2003/0133601 | A1 | 7/2003 | Giger et al. |
| 2003/0161513 | A1 | 8/2003 | Drukker et al. |
| 2003/0174873 | A1 | 9/2003 | Giger et al. |
| 2004/0101181 | A1 | 5/2004 | Giger et al. |
| 2004/0122703 | A1 | 6/2004 | Walker et al. |
| 2004/0147840 | A1 | 7/2004 | Duggirala et al. |
| 2004/0190763 | A1 | 9/2004 | Giger et al. |
| 2004/0193036 | A1 | 9/2004 | Zhou et al. |
| 2004/0247166 | A1 | 12/2004 | Giger et al. |
| 2004/0258310 | A1 | 12/2004 | Giger et al. |
| 2004/0260155 | A1 | 12/2004 | Ciarniello et al. |
| 2005/0020903 | A1 | 1/2005 | Krishnan et al. |
| 2005/0181386 | A1 | 8/2005 | Diamond et al. |
| 2005/0234570 | A1 | 10/2005 | Horsch et al. |
| 2006/0004278 | A1 | 1/2006 | Giger et al. |
| 2006/0018548 | A1 | 1/2006 | Chen et al. |
| 2006/0034508 | A1 | 2/2006 | Zhou et al. |
| 2006/0200010 | A1 | 9/2006 | Rosales et al. |
| 2006/0274928 | A1 | 12/2006 | Collins et al. |
| 2007/0036418 | A1 | 2/2007 | Pan et al. |
| 2008/0101665 | A1 | 5/2008 | Collins et al. |
| 2008/0147445 | A1 | 6/2008 | Rosales et al. |
| 2008/0171916 | A1 | 7/2008 | Feder et al. |
| 2009/0175562 | A1 | 7/2009 | Pan et al. |
| 2011/0028825 | A1 | 2/2011 | Douglas et al. |
| 2011/0142301 | A1 | 6/2011 | Boroczky et al. |
| 2011/0166879 | A1 | 7/2011 | Lee et al. |
| 2011/0170757 | A1 | 7/2011 | Pan et al. |
| 2012/0014578 | A1 | 1/2012 | Karssemeijer et al. |
| 2012/0150034 | A1 | 6/2012 | DeFreitas et al. |
| 2012/0189176 | A1 | 7/2012 | Giger et al. |
| 2012/0215090 | A1 | 8/2012 | Pan et al. |
| 2013/0018271 | A1 | 1/2013 | Mohamad Hani et al. |
| 2013/0289405 | A1 | 10/2013 | Wang et al. |
| 2014/0073907 | A1 | 3/2014 | Kumar et al. |
| 2014/0098099 | A1 | 4/2014 | Welford |
| 2014/0375671 | A1 | 12/2014 | Giger et al. |
| 2015/0117737 | A1 | 4/2015 | Kim et al. |
| 2015/0147460 | A1* | 5/2015 | Manzi .................. B05B 12/122 427/8 |
| 2016/0042511 | A1 | 2/2016 | Chukka et al. |
| 2016/0078624 | A1 | 3/2016 | Giger et al. |
| 2016/0119558 | A1* | 4/2016 | Kaneko ..................... G06T 7/90 348/164 |
| 2017/0124702 | A1* | 5/2017 | Li .......................... G06T 19/003 |

FOREIGN PATENT DOCUMENTS

| | | |
|---|---|---|
| WO | WO-2013/082289 A1 | 6/2013 |
| WO | WO-2013/141974 A1 | 9/2013 |
| WO | WO-2014/169164 A1 | 10/2014 |
| WO | WO-2015/031296 A1 | 3/2015 |

OTHER PUBLICATIONS

Ebenezer, Gemson Andrew and Durga, S. (2015) "Big Data Analytics in Healthcare: A Survey." ARPN Journal of Engineering and Applied Sciences, vol. 10, No. 8, 3645-3650.

Mcsherry, D. (1997) "Avoiding premature closure in sequential diagnosis." Artificial Intelligence in Medicine, 10:269-283.

Reiter, Austin, et al. (2014) "Surgical Structured Light for 3D Minimally Invasive Surgical Imaging." 2014 IEEE/RSJ International Conference on Intelligent Robits and Systems (IROS 2014), Sep. 14-18, 2014, Chicago, IL, USA. (6 pages).

Schrouff, J et al. (2013) "PRoNTo: Pattern Recognition for Neuroimaging Toolbox." Neuroinform vol. 11, 3: 319-37.

Torfeh, Tarraf et al. (2007) "Software Tools Dedicated for an Automatic Analysis of the CT Scanner Quality Control's Images." Proceedings of the SPIE, Medical Imaging. 14 pages. <10.1117/12.707343>. <hal-00326646>.

Xiao M., Soh J., Do T., Meruvia-Pastor O., Sensen C.W. (2010) "Concurrent Visualization of and Mapping between 2D and 3D Medical Images for Disease Pattern Analysis." Supplementary Proceedings of Pattern Recognition in Bioinformatics, 5th IAPR (56) References Cited

OTHER PUBLICATIONS

International Conference, PRIB 2010 in Nijmegen, the Netherlands. 6 pages.

* cited by examiner

MEDICAL ANALYTICS SYSTEM

CROSS-REFERENCES TO RELATED APPLICATION

This application is a continuation of application Ser. No. 16/077,994 filed on Aug. 14, 2018 which is a national stage entry, filed under 35 U.S.C. § 371, of International Application No. PCT/US2017/041735 filed Jul. 12, 2017 which claims priority to U.S. Provisional Application No. 62/361,421, entitled "Diagnostic System," filed Jul. 12, 2016, the disclosure of which is hereby incorporated by reference in its entirety.

TECHNICAL FIELD

Systems and methods are disclosed herein that are related to a medical analytics system including a machine learning model that processes images of a patient for providing at least diagnosis information of the patient.

BACKGROUND

Lung cancer is one of the leading causes of death from cancer, with a current mortality rate of approximately 160,000 deaths per year in the United States. Annual Computed Tomography (CT) screening can result in an approximately 20% reduction in lung-cancer mortality rates for high-risk patients. As such, widespread screening of high-risk lung cancer patients has been generally implemented in medical practice. Though supportive of mortality reduction, a substantial majority of suspicious nodules in the National Lung Screening Trial (NLST) turn out to be negative (e.g., approximately 96%) and screening this population can result in up to approximately $12B of unnecessary procedures, including biopsies, surgeries, and imaging studies on negative patients.

Current approaches to improve diagnostic sensitivity and specificity typically improve one aspect at the expense of the other. For example, using the Lung Imaging Reporting and Data System (Lung-RADS) diagnostic criterion with the NLST dataset, the false positive rate can be reduced. However, Lung-RADS guidelines also reduce the rate of detection (sensitivity). Considering the low survival rate of late stage lung cancer, decreasing the false positive rate alone is not sufficient and early detection is important. Accordingly, a need exists for improved analysis information for diagnosis and treatment of patients.

SUMMARY

Aspects of the current subject matter include a medical analytics system. In one aspect, the medical analytics system performs a computer-implemented method that can include projecting a three-dimensional image of a patient tissue into a plurality of two-dimensional grayscale images and applying at least one transformation algorithm to a first set of two-dimensional grayscale images to generate a first set of transformed two-dimensional grayscale images. The method can further include applying at least one feature algorithm to at least one two-dimensional grayscale image and to each transformed two-dimensional grayscale images of the first set of transformed two-dimensional grayscale images and generating, based on the applying of the at least one feature algorithm to at least one two-dimensional grayscale image and to each transformed two-dimensional grayscale images, a plurality of feature values comprising a feature vector.

Additionally, the method can include projecting the three-dimensional image into a two-dimensional color image and applying at least one color transformation algorithm to a first set of two-dimensional color images to generate a first set of color-transformed two-dimensional grayscale images. In addition, the method can include applying at least one feature algorithm to at least one two-dimensional color image and to each color-transformed two-dimensional grayscale images and generating, based on the applying of the at least one feature algorithm to the at least one two-dimensional color image and to each of the transformed two-dimensional color images, a plurality of color feature values comprising the feature vector. The method can further include collecting patient information and generating, based on the collected patient information, one or more patient values comprising the feature vector. Furthermore, the method can include training a machine learning model based on the feature vector and an associated diagnosis of the patient tissue. The machine learning model can include a classifier having a weighted value assigned to each of the plurality of feature values, the plurality of color feature values, and the patient value. In some implementations, the training of the machine learning model can include determining the weighted values by one or more feature ranking algorithms that rank features by their ability to discriminate between classes.

In some variations one or more of the following features can optionally be included in any feasible combination. The method can further include defining, based on the training, a bio-marker that identifies one or more of the color value, the patient value, and at least one of the plurality of feature values. The bio-marker can be part of the trained classifier for determining a diagnosis of an undiagnosed tissue captured in an undiagnosed three-dimensional image. The diagnosis can include whether the undiagnosed tissue is malignant or benign. The undiagnosed tissue can include lung tissue or breast tissue, or any number of other types of abnormalities that can be identified in medical imagery. The three-dimensional image can include a part of a captured three-dimensional image generated by a three-dimensional imaging system. The three-dimensional image can be projected onto at least two different dimensional planes thereby generating at least two different two-dimensional grayscale images.

In some embodiments, the medical analytics system performs a computer-implemented method that can include processing, using a trained machine learning model, a feature vector generated from an image file. The trained machine learning model can be trained to determine at least one of a diagnosis of tissue captured in an image file. The diagnosis can include whether the tissue is benign or malignant. The method can further include providing, as an output by the trained machine learning model, at least one of the diagnosis and a treatment information related to the diagnosis.

In some embodiments, the medical analytics system performs a computer-implemented method that can include receiving, at processor associated with medical analytics system, a patient image capturing tissue and generating, at the processor and using the patient image, a feature vector. The computer-implemented method can further include analyzing, using the machine learning model of the medical analytics system, the feature vector to at least diagnose the tissue captured in the patient image and displaying, on the user interface, at least the diagnosis of the tissue. The diagnosis can include one or more of a type of disease, a type of cancer, a percentage risk associated with the diagnosis, a treatment information, and a percentage of likely outcomes.

Systems and methods consistent with this approach are described as well as articles that comprise a tangibly embodied machine-readable medium operable to cause one or more machines (e.g., computers, etc.) to result in operations described herein. Similarly, computer systems are also described that may include a processor and a memory coupled to the processor. The memory may include one or more programs that cause the processor to perform one or more of the operations described herein.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Certain exemplary embodiments will now be described to provide an overall understanding of the principles of the systems, processes, and methods disclosed herein. One or more examples of these embodiments are illustrated in the accompanying drawings. Those skilled in the art will understand that the systems, processes, and methods specifically described herein and illustrated in the accompanying drawings are non-limiting exemplary embodiments and that the scope of the present invention is defined by the claims. The features illustrated or described in connection with one exemplary embodiment may be combined with the features of other embodiments. Such modifications and variations are intended to be included within the scope of the present invention.

Systems and methods of a medical analytics system are provided herein. The medical analytics system can include a machine learning model for processing patient tissue images for either training the machine learning model or for clinical use, such as for providing at least diagnosis information of patient tissue captured in an image (e.g., x-ray image, computed tomography (CT) scan, microscopy, other types of digital medical imagery, etc.). Implementations of the medical analytics system can further include a user interface that is configured to allow a user to interact with the patient image (e.g., select areas of interest within the image) for assisting with diagnosing at least a part of the tissue captured in the patient image. Such diagnosis can include, for example, malignant or benign tumors in various types of tissue (e.g., breast tissue, lung tissue), physical abnormalities (e.g. emphysema, Alzheimer's disease, cardiovascular disease, etc.), and/or physical trauma (e.g. head injury, wound healing, etc.). As will be described in greater detail below, the medical analytics system of the present disclosure can provide improved diagnosis and treatment of tissue thereby improving patient care and patient longevity. Furthermore, as described herein, a diagnosis can include information directly identifying a disease or condition of the patient and/or a diagnosis can include one or more information that can assist a clinician with identifying the disease or condition of the patient. For example, such information for assisting the clinician with identifying the disease or condition can include a percentage of likeliness that an analyzed image of the patient includes a particular disease or condition. However, various other types of information for assisting the clinician with identifying a disease or condition of the patient is within the scope of this disclosure.

The medical analytics system described herein can include a processing system that generates a feature vector from an image capturing tissue (e.g., lung tissue, breast tissue, etc.) of a patient and from information associated with the patient (e.g., smoking history, age, medical history, etc.). Such a feature vector can be used by the medical analytics system to either train a machine learning model of the medical analytics system or for clinical use, such as for assisting with diagnosing the tissue captured in the image, as will be described in greater detail below.

In some implementations, the medical analytics system can include a machine learning model that can be trained to provide improved diagnosis of various types of tissue. For example, the machine learning model can train a classifier configured to analyze feature vectors generated by the processing system for diagnosing various conditions of the patient tissue captured in the image associated with the feature vector, such as types of tumors (e.g., malignant, benign), cardiovascular disease, emphysema, liver cirrhosis, kidney disease, Alzheimer's disease, osteoarthritis and other diseases of the bone and joints, physical trauma, etc.

In some implementations the medical analytics system can include a user interface that allows a user, such as a clinician, to interact with the patient image for analyzing various parts or features within the image. For example, the user interface of the medical analytics system can allow the user to select a part of the image that the medical analytics system can then generate a feature vector from and run the feature vector through the machine learning model, such as through the trained classifier, to thereby provide the user with a variety of clinically useful information, including for diagnosing patient tissue.

Figure 1:
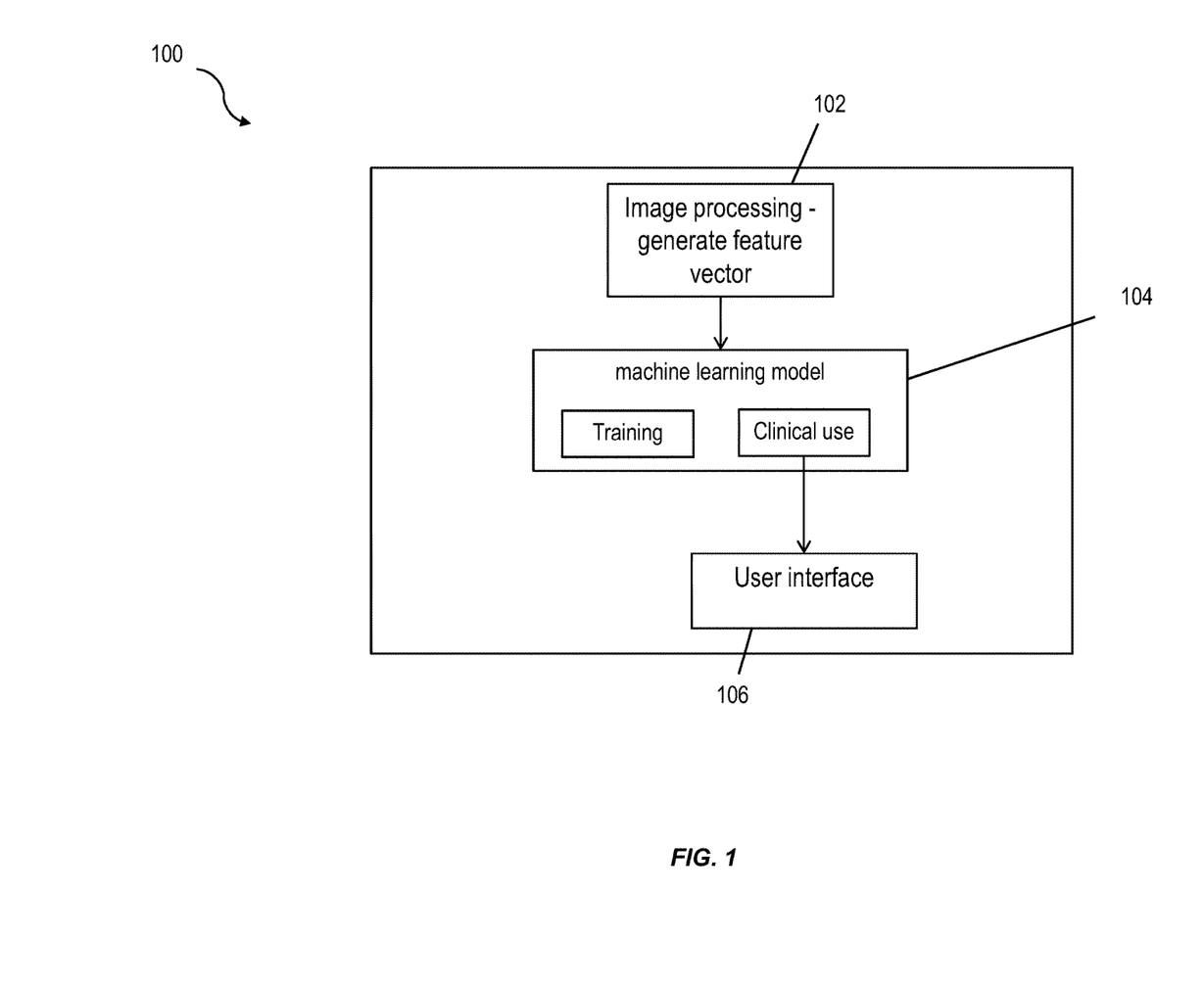
FIG. 1 shows a diagram illustrating a medical analytics system consistent with implementations of the current subject matter.

FIG. 1 illustrates an embodiment of a medical analytics system 100 that includes an image processing system 102, a machine learning model 104 that can be either trained or used for clinical use, and a user interface 106. As will be described in greater detail below, the image processing system 102 can generate feature vectors from patient tissue images that can be used to train the machine learning model 104. The machine learning model 104 can be trained to provide useful and accurate diagnosis information when analyzing feature vectors generated for clinical use. Such diagnosis information, which can include percentages of likelihood of the presence of a disease, treatment information, etc., can be displayed by the user interface 106 of the medical analytics system 100, as will be described in greater detail below.

Figure 2:
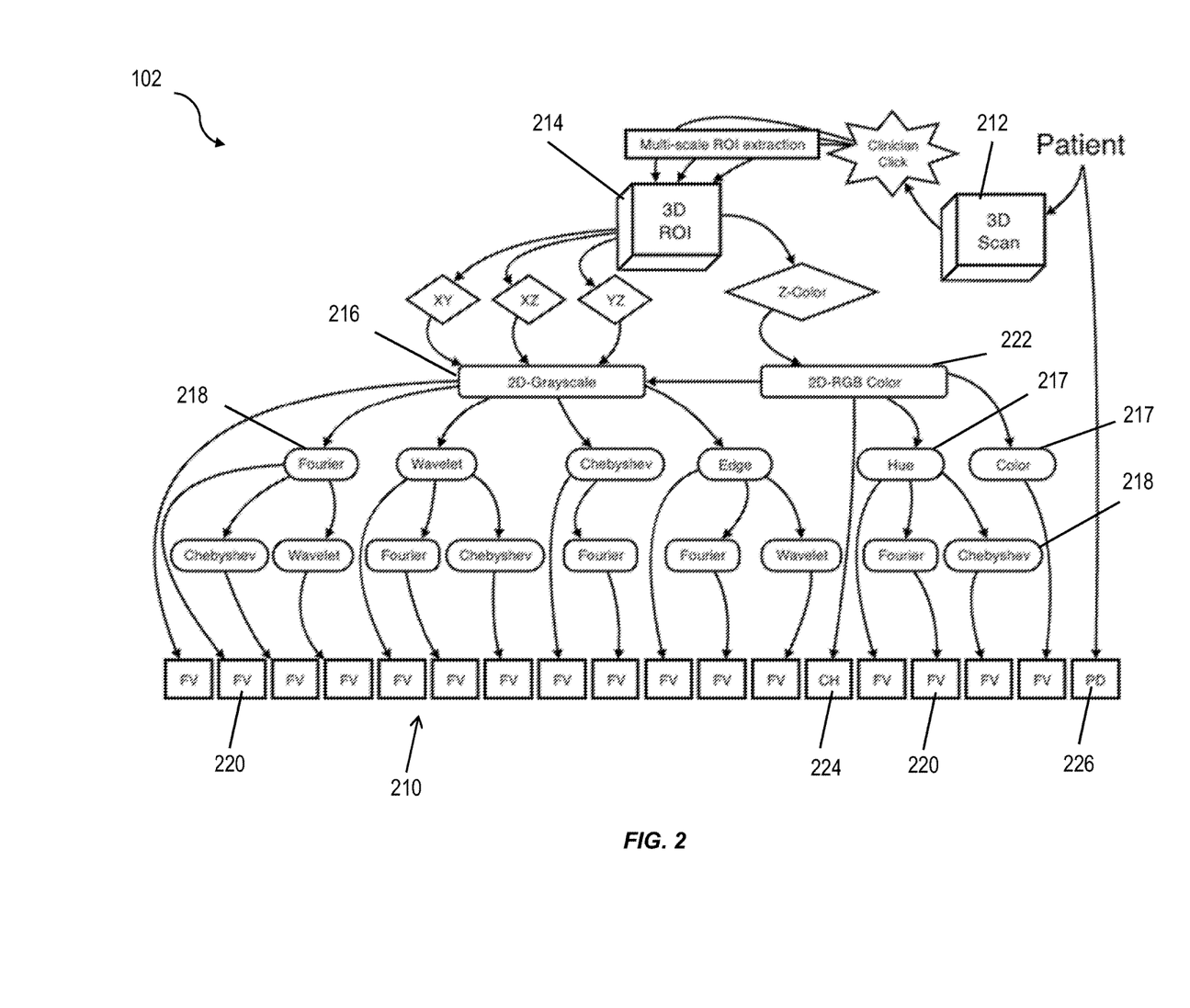
FIG. 2 shows a diagram illustrating processing of a patient tissue image and patient information to generate a feature vector that is used by the medical analytics system of FIG. 1.

FIG. 2 illustrates an embodiment of the processing system 102 of the medical analytics system 100, including processes and methods associated with generating a feature vector 210 from an image 212 (e.g., x-ray image, CT scan image, etc.) capturing a patient tissue (e.g., lung tissue, breast tissue, etc.). The image 211 used for generating the feature vector 210 can include all or a part of the image 211 taken of the patient. For example, a part of the image 211 can be selected for processing by the processing system 102 for generating the feature vector 210. As shown in FIG. 2, a part of the image 211 can be selected, such as by a user (e.g., clinician), which can be extracted to generate a three-dimensional (3D) region of interest rendering 214. As will be described in greater detail below, the user interface 106 of the medical analytics system 100 can allow a user to select a part or region of interest of the patient image 212 for analysis by the medical analytics system 100. Such selected part of the image 212 can be processed by the processing system 102 to thereby generate a feature vector 210 associated with the selected part of the image 212. This can allow a user to select specific parts of the image 212 for analysis, such as to analyze abnormal features displayed in the image 212.

As shown in FIG. 2, the processing system 102 can receive the image 212 and/or the selected part of the image to thereby generate the 3D region of interest rendering 214. Although the following example is described relative to processing the 3D region of interest rendering 214, the entire image 212 can also be used without departing from the scope of this disclosure. As shown in FIG. 2, the 3D region of interest rendering 214 can be projected onto one or more dimensional planes (e.g., XY plane, XZ plane, YZ plane) to thereby generate at least one two-dimensional (2D) grayscale rendering 216 of the 3D region of interest rendering 214. For example, the 3D region of interest rendering 214 can be projected onto the XY plane, XZ plane, and YZ plane to generate three different 2D grayscale renderings 216. In addition, other non-orthogonal projections can also be generated at angles other than 90 degrees thereby creating a multitude of 2D views of the original 3D scan. In addition to these 2D grayscale projections, 2D color projections 222 can be used to represent information in the 3D grayscale image as 2D. The combination of 2D grayscale and color views can provide a more accurate and complete representation of the information present in 3D without having to develop or use 3D-specific feature extraction algorithms. The 2D grayscale renderings 216 can then be transformed at least once using one or more transform algorithms 218. Such transform algorithms 218 can include any number of a variety of transform algorithms, such as Fourier, Wavelet, Chebyshev, etc., without departing from the scope of this disclosure. These transform algorithms 218 can transform a 2D grayscale image into another 2D grayscale image with different content (e.g., transformed 2D grayscale image) as their outputs. Furthermore, the 2D grayscale images, whether original or transformed, can be treated equivalently by a set of feature algorithms, which convert input images (e.g., 2D grayscale rendering 216, transformed 2D grayscale image, etc.) into a set of numerical descriptions of image content.

Combining transforms can generate a multiplier for the number of ways an original 2D image can be represented using other 2D images. The more ways a 2D image can be run through the transform algorithms, the more diverse the image features that can be represented by the set of feature algorithms. Diversifying the image content that can be quantified numerically can ensure that a greater variety of image changes are analyzed and processed by the analytics system 100.

For example, a transform algorithm 218 can be applied to the 2D grayscale renderings 216 thereby generating a transformed 2D grayscale image. The same or different transform algorithm 218 can then be applied to the transformed 2D grayscale image to thereby generate another transformed 2D grayscale image. The transformed 2D grayscale images can then have the set of feature algorithms applied for generating a plurality of feature values 220 in the feature vector 210. In addition, the 2D grayscale renderings 216 can have the set of feature algorithms directly applied (e.g., no transform algorithm applied) to thereby generate feature values 220 or the 2D grayscale renderings 216 can have a single transform algorithm 218 applied before applying the set of feature algorithms for generating a feature value 220. In some embodiments, the 2D grayscale renderings 216 have more than two transform algorithms 218 applied to assist with generating feature values 220. As shown in FIG. 2, the feature vector 210 can include a plurality of feature values 220 generated from the set of feature algorithms being applied to the 2D grayscale renderings 216 and/or transformed 2D grayscale renderings. For example, the feature algorithms used to generate feature values 220 can include one or more of the following: edge features, Otsu object features, inverse-Otsu object features, Multiscale Histograms, Pixel Intensity Statistics, Haralick Textures, Tamura Textures, Gabor Textures, Chebyshev Coefficients, Zernike Coefficients, Chebyshev-Fourier Coefficients, Comb Moments, Radon Coefficients, Fractal Features, Gini Coefficient, etc.

For example, each feature algorithm (e.g. Otsu features) can read a 2D image and produces a small number of the numerical features that make up feature values 220. As such, each feature value 220 can be a numerical value representing a quantity for a very specific type of image content. The difference between one feature value 220 and another can be the transforms used to generate the input images for its component algorithms. For example, Otsu( ) features can be from the raw image, and Otsu(Fourier( )) features can be from the Fourier transform of the raw image. Furthermore, Otsu(Fourier( ))[11] can be the 11th value output by the Otsu feature algorithm run on the Fourier transform of the raw image. The Otsu algorithm can produce the same number of values each time it is run. Each value can define something different and specific. For instance, the 11th value could always mean the number of shapes found with all pixel values above an Otsu threshold.

The feature values 210 can include a variety of indicators, such as a number or value (e.g. 12.63987). For example, each feature value 210 can be a statistic or a measurement of the quantity of a particular texture. The type of feature value 210 can depend upon the algorithm that produced it.

As shown in FIG. 2, the 3D region of interest rendering 214 can be processed by the processing system 102 to generate a 2D color rendering 222 of the 3D region of interest rendering 214. A color transform algorithm 217 can be applied to the 2D color rendering 222 thereby generating a color-transformed 2D grayscale image. Examples of color transform algorithms 217 that can read a 2D color image and transform it to a 2D grayscale image can include one or more of the following: using the color wavelength as the grayscale value; converting from RGB values to HSV values and using the Hue (H) as the grayscale value; and/or using the luminosity of the color as the grayscale value. A transform algorithm 218 can then be applied to the color-transformed 2D grayscale image to thereby generate another transformed 2D grayscale image, which can then have a same or different set of feature algorithms applied for generating a plurality of feature values 220 in the feature vector 210. In some implementations, the feature algorithms can be applied to the color-transformed 2D grayscale image directly without one or more intervening transform algorithms 218. In addition, the 2D color rendering 222 can have a set of color feature algorithms applied for generating color feature values 224. Examples of these color-feature algorithms include color histograms, which count the number of pixels represented by a particular color, or other color feature algorithms that use the color information in the 2D color rendering 222. The 2D color rendering 222 can have one or more color transform algorithms 217 applied thereto prior to applying the feature algorithms for generating a feature value 220. In some embodiments, the 2D color rendering 222 can have more than two color transform algorithms 217 applied. As shown in FIG. 2, the feature vector 210 can include a plurality of feature values 220, as well as and at least one color feature value 224 generated from a feature algorithm applied directly to the 2D color rendering 222.

As shown in FIG. 2, the feature vector 210 can include one or more patient values 226 that can be determined from on one or more of a variety of information related to the patient associated with the image 212. For example, such information can include smoking history, medical history, age, etc. In some implementations, a patient value 226 can be generated, at least in part, based on smoking history of the patient. For example, smoking history can be represented as pack-years (e.g., number of pack-a-day per year, so 2.0 would be 1 year of 2-packs a day or 2 years of 1 pack a day). As such, the patient value 226 can be a single number or value, which can be the same format as other feature values 220 originating from image content. Other patient values can include age (e.g., 32.5), systolic blood pressure (e.g., 180.0), etc.

For example, once a feature vector 210 has been generated by the processing system 102, the feature vector can be used by the machine learning model 104 to either train the machine learning model 104 or diagnose tissue associated with the feature vector 210. The machine learning model 104 can include any of a variety of neural networks or other classifiers such as WND5, Random Forrest, Support Vector Machines, Nearest-Neighbors, etc.

Figure 3:
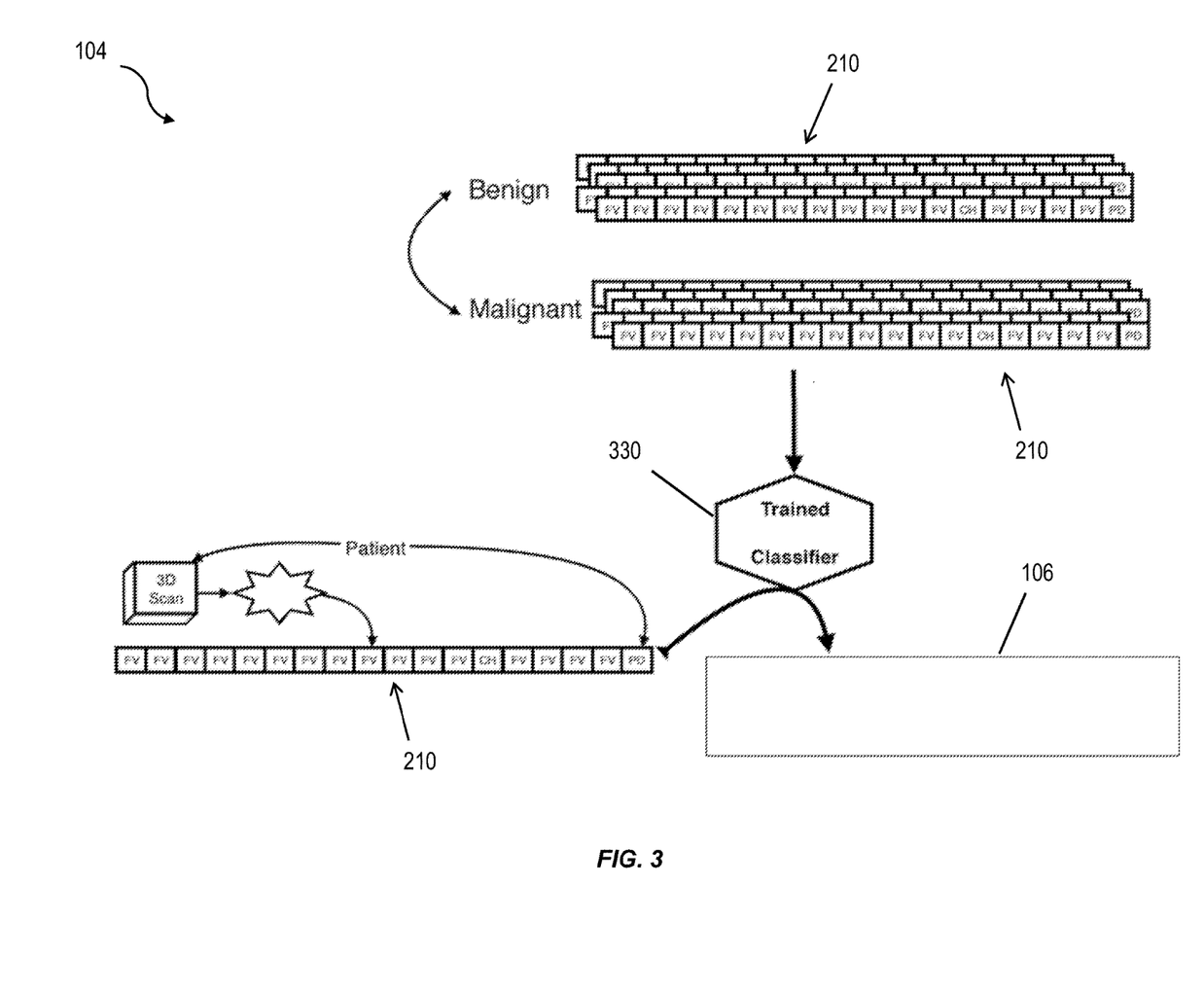
FIG. 3 shows a diagram illustrating training a machine learning model of the medical analytics system of FIG. 1 using at least feature vectors generated by the process illustrated in FIG. 2.

FIG. 3 illustrates various aspects and processes associated with the machine learning model 104. For example, the machine learning model 104 can be trained by dividing up generated feature vectors 210 into two or more groups. The first group can include all feature vectors associated with tissue that was diagnosed as benign, for example. The second group can include all feature vectors associated with tissue that was diagnosed as malignant, for example. The machine learning model 104 can include at least one algorithm that can rank the individual feature values 220, color values 224, and patient values 226 by their power to discriminate between two or more classes (groups). Such feature ranking algorithms include the Fisher discriminant, mRMR, etc. In addition, other algorithms can be used that project the features into a different lower-dimensionality space, such as principal component analysis (PCA), linear discriminant analysis (LDA), etc. The result of feature ranking or projection is a reduced set of features that are selected for their discriminative power in a specific problem as defined, for example, by the subdivision of feature vectors into groups (e.g. benign vs. malignant). A classifier 330 can be trained on one or more of the selected feature values 220, color values 224, and patient value 226. The selected features can also be weighted by (e.g., multiplied by) the weights (e.g., rank scores) from the feature ranking algorithms prior to using them to train classifiers. Once trained, the classifier 330 can be used to analyze feature vectors 210 generated during clinical use, such as after these feature vectors have been reduced and possibly weighted by the same mechanisms as used during training.

For example, the machine learning model 104 can analyze a feature vector associated with an undiagnosed tissue captured in an image. As shown in FIG. 3, the trained classifier 330 of the machine learning model 104 can analyze this feature vector 210 associated with the undiagnosed tissue to thereby provide an analysis of the tissue. The trained machine learning model 104 includes a trained classifier 330 and a biomarker that defines which feature values 220, color values 224, and/or patient values 226 get included for performing a specific analysis (e.g., tumor type in lung tissue, etc.). For example, the biomarker can include a set of selected image features and their corresponding weights. For example, Table 1 illustrates an example biomarker for diagnosing lung tissue malignancy. The feature names listed in Table 1 include names of the feature algorithms described above, along with the names of the transform algorithms used to generate the transformed 2D grayscale image the feature algorithm operated on in parentheses. Additionally, an index of the specific output value of the several values output by the feature algorithm when run is shown in square brackets. The distribution of weight values assigned to the indicated features by the feature ranking algorithms during different training sessions is shown in the table as the minimum and maximum of the weight range, the mean, and the standard deviation. For example, each individual random trial done for cross-validation of the training model can generate one set of weights (e.g., specific values generated by the feature ranking algorithms). The random trials can generate a distribution of weights (e.g., specific values) for each feature. For example, each feature can have its own weight. The weight can be applied to each corresponding feature by multiplying the associated feature value by the weight. Table 1 below illustrates an example of the distribution of weight values across several random trials used in cross-validating the training machine learning model. Table 1 shows statistics that can indicate consistency of relative importance of one or more features over a plurality of trainings, including based on random sub-selections of a large set of training data. For example, a feature with a small standard deviation relative to its mean can indicate that the feature is highly weighted repeatedly and consistently across many sub-selections, thus justifying its importance and inclusion in a biomarker for the particular imaging problem (e.g. benign/malignant for lung nodules in CT scans).

TABLE 1

| Feature Name | min | max | mean | std Dev |
|---|---|---|---|---|
| Chebyshev Coefficients (Wavelet (0)) [12] | 0.479 | 0.683 | 0.586 | 0.038 |
| Pixel Intensity Statistics (Chebyshev (0)) [3] | 0.462 | 0.680 | 0.567 | 0.040 |
| Chebyshev-Fourier Coefficients (Color Transform (0)) [0] | 0.441 | 0.664 | 0.549 | 0.038 |
| Chebyshev-Fourier Coefficients (0) [0] | 0.441 | 0.664 | 0.549 | 0.038 |
| Pixel Intensity Statistics (Chebyshev (Wavelet (0))) [4] | 0.420 | 0.624 | 0.520 | 0.036 |
| Haralick Textures (Chebyshev (Wavelet (0))) [22] | 0.410 | 0.604 | 0.513 | 0.034 |
| Multiscale Histograms (0) [8] | 0.375 | 0.588 | 0.489 | 0.042 |
| Multiscale Histograms (Color Transform (0)) [8] | 0.375 | 0.588 | 0.489 | 0.042 |
| Haralick Textures (Chebyshev (0)) [20] | 0.391 | 0.576 | 0.488 | 0.034 |
| Haralick Textures (Chebyshev (Wavelet (0))) [10] | 0.395 | 0.580 | 0.487 | 0.033 |
| Multiscale Histograms (Color Transform (0)) [3] | 0.370 | 0.568 | 0.470 | 0.037 |
| Multiscale Histograms (0) [3] | 0.370 | 0.568 | 0.470 | 0.037 |
| Zernike Coefficients (Fourier (Wavelet (0))) [64] | 0.389 | 0.565 | 0.466 | 0.031 |
| Pixel Intensity Statistics (Chebyshev (0)) [4] | 0.359 | 0.553 | 0.458 | 0.032 |
| Haralick Textures (Chebyshev (Wavelet (0))) [8] | 0.364 | 0.533 | 0.453 | 0.030 |
| Haralick Textures (Chebyshev (0)) [8] | 0.367 | 0.552 | 0.451 | 0.033 |
| Zernike Coefficients (Fourier (Wavelet (0))) [48] | 0.369 | 0.539 | 0.448 | 0.030 |
| Zernike Coefficients (Fourier (Wavelet (0))) [62] | 0.353 | 0.520 | 0.429 | 0.029 |
| Multiscale Histograms (0) [15] | 0.329 | 0.522 | 0.428 | 0.038 |
| Multiscale Histograms (Color Transform (0)) [15] | 0.329 | 0.522 | 0.428 | 0.038 |
| Zernike Coefficients (Fourier (Wavelet (0))) [70] | 0.349 | 0.516 | 0.426 | 0.029 |
| Haralick Textures (Fourier (0)) [26] | 0.333 | 0.531 | 0.426 | 0.033 |
| Haralick Textures (Fourier (Wavelet (0))) [22] | 0.346 | 0.497 | 0.422 | 0.027 |
| Tamura Textures (Wavelet (0)) [3] | 0.341 | 0.502 | 0.421 | 0.031 |
| Haralick Textures (Chebyshev (Wavelet (0))) [14] | 0.337 | 0.508 | 0.419 | 0.030 |
| Zernike Coefficients (Fourier (Wavelet (0))) [55] | 0.343 | 0.502 | 0.418 | 0.028 |
| Pixel Intensity Statistics (Fourier (Chebyshev (0))) [0] | 0.327 | 0.515 | 0.416 | 0.033 |
| Pixel Intensity Statistics (0) [1] | 0.337 | 0.502 | 0.414 | 0.032 |
| Pixel Intensity Statistics (Color Transform (0)) [1] | 0.337 | 0.502 | 0.414 | 0.032 |
| Haralick Textures (Chebyshev (0)) [24] | 0.331 | 0.482 | 0.413 | 0.031 |
| Zernike Coefficients (Fourier (Wavelet (0))) [24] | 0.340 | 0.502 | 0.412 | 0.029 |
| Zernike Coefficients (Fourier (Wavelet (0))) [58] | 0.334 | 0.495 | 0.409 | 0.031 |
| Haralick Textures (Chebyshev (Wavelet (0))) [18] | 0.322 | 0.506 | 0.405 | 0.033 |
| Multiscale Histograms (Fourier (Wavelet (0))) [16] | 0.310 | 0.490 | 0.404 | 0.030 |
| Haralick Textures (Fourier (0)) [24] | 0.317 | 0.498 | 0.403 | 0.031 |
| Zernike Coefficients (Fourier (Wavelet (0))) [57] | 0.313 | 0.487 | 0.401 | 0.030 |
| Multiscale Histograms (Fourier (Chebyshev (0))) [10] | 0.295 | 0.483 | 0.400 | 0.032 |
| Chebyshev-Fourier Coefficients (Color Transform (0)) [1] | 0.295 | 0.498 | 0.400 | 0.033 |
| Chebyshev-Fourier Coefficients (0) [1] | 0.295 | 0.498 | 0.400 | 0.033 |
| Haralick Textures (Chebyshev (Wavelet (0))) [0] | 0.340 | 0.467 | 0.398 | 0.024 |
| Zernike Coefficients (Fourier (Wavelet (0))) [51] | 0.328 | 0.481 | 0.397 | 0.028 |
| Pixel Intensity Statistics (Chebyshev (0)) [2] | 0.310 | 0.496 | 0.397 | 0.032 |
| Pixel Intensity Statistics (Fourier (Chebyshev (0))) [1] | 0.316 | 0.480 | 0.397 | 0.030 |

TABLE 1-continued

| Feature Name | min | max | mean | std Dev |
|---|---|---|---|---|
| Pixel Intensity Statistics (0) [0] | 0.314 | 0.486 | 0.396 | 0.030 |
| Pixel Intensity Statistics (Color Transform (0)) [0] | 0.314 | 0.486 | 0.396 | 0.030 |
| Pixel Intensity Statistics (Fourier (0)) [4] | 0.314 | 0.486 | 0.396 | 0.030 |
| Radon Coefficients (Fourier (0)) [3] | 0.310 | 0.490 | 0.395 | 0.031 |
| Pixel Intensity Statistics (Wavelet (Fourier (0))) [3] | 0.313 | 0.481 | 0.393 | 0.029 |
| Zernike Coefficients (Fourier (Wavelet (0))) [71] | 0.328 | 0.485 | 0.392 | 0.028 |
| Inverse-Otsu Object Features (0) [11] | 0.302 | 0.490 | 0.392 | 0.034 |
| Zernike Coefficients (Fourier (Wavelet (0))) [34] | 0.319 | 0.476 | 0.387 | 0.028 |
| Zernike Coefficients (Fourier (Wavelet (0))) [33] | 0.319 | 0.468 | 0.387 | 0.026 |

After the machine learning model has been trained, the user interface 106 can display a user-selected area of the image for classification and analysis. The user interface 106 can provide similarity measurements to the set of malignant, diseased or otherwise abnormal samples that it was trained with. Along with a similarity score, the user interface 106 can display one or more of the most similar cases, such as based on a database accessible by or included in the medical analytics system 100. For example, the database can include images, demographic data, as well as other information about cases that were or were not used in training (for e.g. the cancer subtype determined from the histopathology report of the training lesion when it was biopsied).

Figure 4:
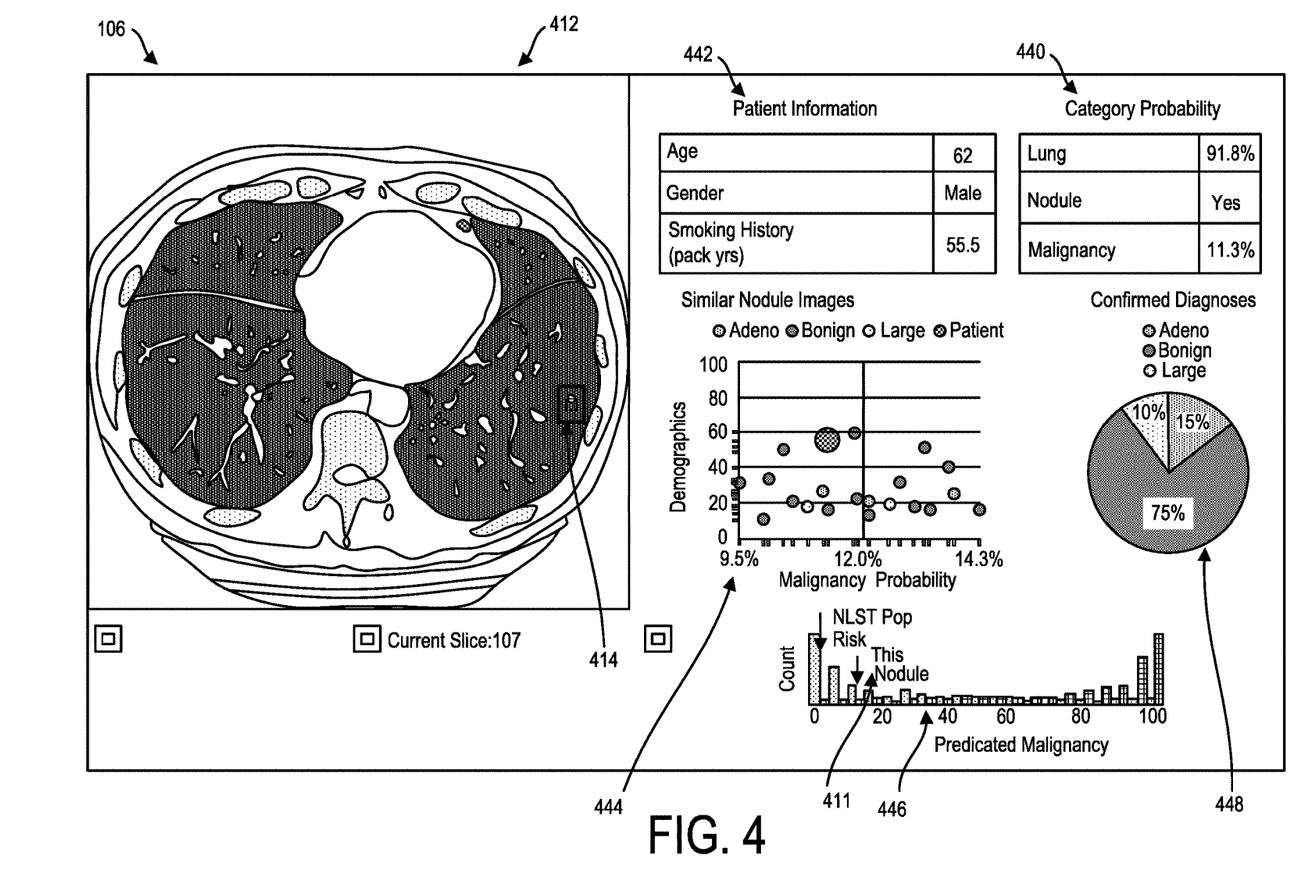
FIG. 4 shows an example user interface view illustrating an output provided by the medical analytics system of FIG. 1.

FIG. 4 illustrates an example output displayed on a display by the user interface 106. As shown in FIG. 4, the user interface can display the image 412 capturing patient tissue (e.g., lung tissue, breast tissue, etc.) and allow the user to select a region or area 414 of the image 412 (e.g., size or position a perimeter around the area 414) for analysis to receive a diagnosis and/or information assisting with diagnosing the tissue. After the region 414 of the image 412 has been selected, the medical analytics system 100 can generate a feature vector 210 that gets analyzed by the machine learning model 104, as described above. The analysis by the machine learning model 104 can provide the user interface 106 with a variety of information for displaying to the user. For example, as shown in FIG. 4, the user interface 106 can include probabilities produced by the classifier, which can be interpreted as similarities to the indicated class. For example, FIG. 4 shows that the probability that the image region indicated on the left with a red square belongs to the group of training images constituting the malignant class is 11.3 percent. Patient information 442 can also be displayed by the user interface. Such patient information can include the patient's age, gender, smoking history, etc.

The user interface can also display a variety of graphical representations. For example, a first graphical representation 444 can show a diagnosis probability compared to other similar images (e.g., the largest circle representing the current case being analyzed), and a second graphical representation 446 can show the effectiveness of training as a dual histogram, with benign/normal samples in one color (e.g., red) and malignant/abnormal/diseased samples in another color (e.g., blue). The horizontal axis can indicate the similarity score obtained for the training samples in cross-validation, and the vertical axis can indicate the number of times each similarity range (e.g., bin) was observed. The separation of the benign cases from the malignant cases in such a dual histogram can indicate the effectiveness of training. Displaying the probability of the case being reviewed on the same horizontal axis (white arrow 411 in FIG. 4) can represent how the case being analyzed relates to the images and data the machine learning model 104 was trained with. This can also give an indication of the confidence with which the current case can be evaluated. If the case is in an area where a large number of training cases were correctly identified (e.g., the histogram peaks), then more confidence can be given to the evaluation compared to an area where the number of correct cases are lower (e.g., between two histogram peaks). A third graphical representation 448 (e.g., a pie chart) provided by the user interface 106 can include distributions of specific sub-types of malignancy/abnormality as determined by follow-up studies of the training cases most similar to the case being analyzed.

The medical analytics system 100 can provide a number of benefits and functions that can improve diagnosis and treatment of patients. For example, in some implementations, the medical analytics system 100 can provide at least the following: 1) display similar cases from a reference database in lung cancer based on image and patient parameters; 2) provide summary statistics of similar cases including percentage of cancers, disease characterization, follow-up procedures, treatments and outcomes; 3) provide differences between the current patient and similar patients in terms of image and patient parameters; 4) provide analysis of the contribution of image and patient features in determining similarity to reference database.

In some implementations, the medical analytics system 100 can compare identified cancerous tissue to one or more stored images contained in a database. The diagnostic system identifies matches between the identified cancer tissue in the patient's image and at least one stored image in the database to determine at least one characteristic (e.g., type of cancer, survival rate, etc.) of the identified cancer. In addition, the system compares at least one risk factor and/or characteristic of the patient with at least one stored risk factor and/or stored characteristic of other patients contained in the database. Such comparing of risk factors and/or patient characteristics allow the medical analytics system 100 to identify a variety of either treatments or possible additional ailments that may or may not be associated with the identified tissue thereby possibly leading to further medical screening to treat such ailments.

In some implementations, the medical analytics system 100 can determine and provide one or more of at least three categories of information to a user, such as 1) provides an assessment of risks associated with one or more diseases based on an image of the user (e.g., x-ray, CAT scan) and characteristics of the patient (e.g., smoking frequency, age, etc.); 2) provides, based on the assessment of risks, the potential value of follow-up procedures for the patient (e.g., biopsy); and 3) provides, based on the assessed risks, a valuation or assessment of an optimal treatment or treatment plan (e.g., type of chemotherapy, surgery). The medical analytics system 100 described herein can therefore not only provides improved screening and identification of cancerous (or potentially cancerous) tissue of interest of a patient, but can also screen and identify additional ailments as a result of comparing patient information with information stored on a database, thus improving medical care. In addition, such identifications of tissue can also include further stratification of information (e.g., not only is the cancer identified, but also any sub-types of cancer that can appear in the patient's body over the next several months and/or years). Furthermore, some implementations of the medical analytics system 100 disclosed herein can be used for detecting and providing assessments, follow-up procedures, and valuations for treatment for any number of a variety of diseases and/or ailments (e.g., cardiovascular, neurological, and gastro-intestinal diseases and/or ailments). The medical analytics system 100 can also include a cloud-based system where information can be stored, transmitted, and/or received through the cloud-based system. For example, physicians can directly interact with a cloud-based medical analytics system 100 for performing any of the features and functions described herein.

In some implementations, the medical analytics system 100 includes a processor configured to perform image processing, pattern recognition, and machine learning algorithms. The medical analytics system 100 can further include a database or library of reference image cases and a viewing software that interfaces with standard image viewing software. The library can be expanded on an ongoing basis, such as with real-world clinical data that can improve its applicability (e.g., to a more diverse set of patients and/or outcomes).

In some implementations, image features of the images can be analyzed by the medical analytics system 100 using histogram statistics, edge features, texture features, object characteristics, and/or orientation moments, which can be calculated in combination with either signal filters or transforms of the image data, such as in different domains. This multi-layered approach can capture various types of features that can be understood visually and many more that themselves or in combination are either too subtle or complex to be recognized by human observation. In some applications, these are computed natively in three dimensions while in others the feature computation is performed via cross-correlation between colors with the image depth represented. Features can be computed on a series of anatomical compartments, including the full scan, sub-regions isolated via segmentation techniques, and user-indicated locations. Segmentation for anatomical compartments (i.e., lung and mediastinum) can be performed using a combination of various methods. Image co-registration over time can also be used to include features related to progression. In combination, for example, there can be over eight thousand computed features used as input for classifications such as risk-assessment.

For example, once the above features have been computed, their predictive rank can be evaluated in the training phase by the machine learning model 104 that weights their contribution to known outcome measures (e.g., malignancy). The result can be an n-dimensional vector space with node values. Comparative placement of new imagery/cases, can be continuously compared. Thus any new statistical summary of similar cases can be an extension of an image search capability with a new case compared across one or more dimensions. This approach can allow for multiple areas of sub-segregation and adaptive comparisons as new cases (and outcomes) are added to the library.

The medical analytics system 100 can utilize the library of reference image cases, for example, as follows: 1) extract image patterns using pattern recognition algorithms and transforms (e.g., approximately 4,000 computations) on the image and image subsets, 2) use the machine learning model 104 to relate extracted image patterns and patient information to known patient outcomes.

Some of the following technologies can be implemented in the medical analytics system 100 described herein: 1) Segmentation; 2) Registration; 3) Feature extraction (CHRM); 4) Dimensionality reduction/Pattern detection (WND); and 5) Statistical machine-learning. In some implementations, the processor of the medical analytics system 100 can execute viewing software (e.g., via the user interface 106) and use one or more of the feature extraction (CHRM) and dimensionality reduction/pattern detection (WIND) algorithms to identify corresponding summary statistics of the selected node for malignancy and disease characterization from similar cases. The viewing software analysis can use a contribution of the image and patient features to determine (e.g., calculate) the similarity to the reference database. Key Diagnostic Indicators can include a plurality of parameters that the medical analytics system 100 has determined are important in determining similarity with similar case. For example, the top 20 parameters can be included in the Key Diagnostic Indicators. The determined weighting factor can also be displayed.

The user interface 106 can be used to compile patient image cases that are similar to the patient under examination. A summary of image and patient details from similar cases can be presented for clinicians to compare with their current patient in order to provide additional information when making medical related decisions. This analytics tool can be used by providers to assess the preliminary risk of cancer (e.g., lung cancer) in patients that have, for example, undergone low-dose CT. For example, the analytics tool can be used by Radiologists and Oncologists to assess preliminary risk through a comparison with similar reference cases.

The medical analytics system 100 can provide look-up' functionality spanning past clinical research studies (e.g., PLCO, NLST) and clinical image archives using, for example, documented outcomes as the standard by which measurements, search capabilities, and summary graphs are provided. The user interface 106 can allow the clinician to see the results of these analytics and can display images directly from a PACS system, as well as facilitate clinician assessment of a specific patient. In some implementations, the final assessment or diagnosis can be left to the clinician, who can be instructed to review images on an approved PACS system.

Figure 5:
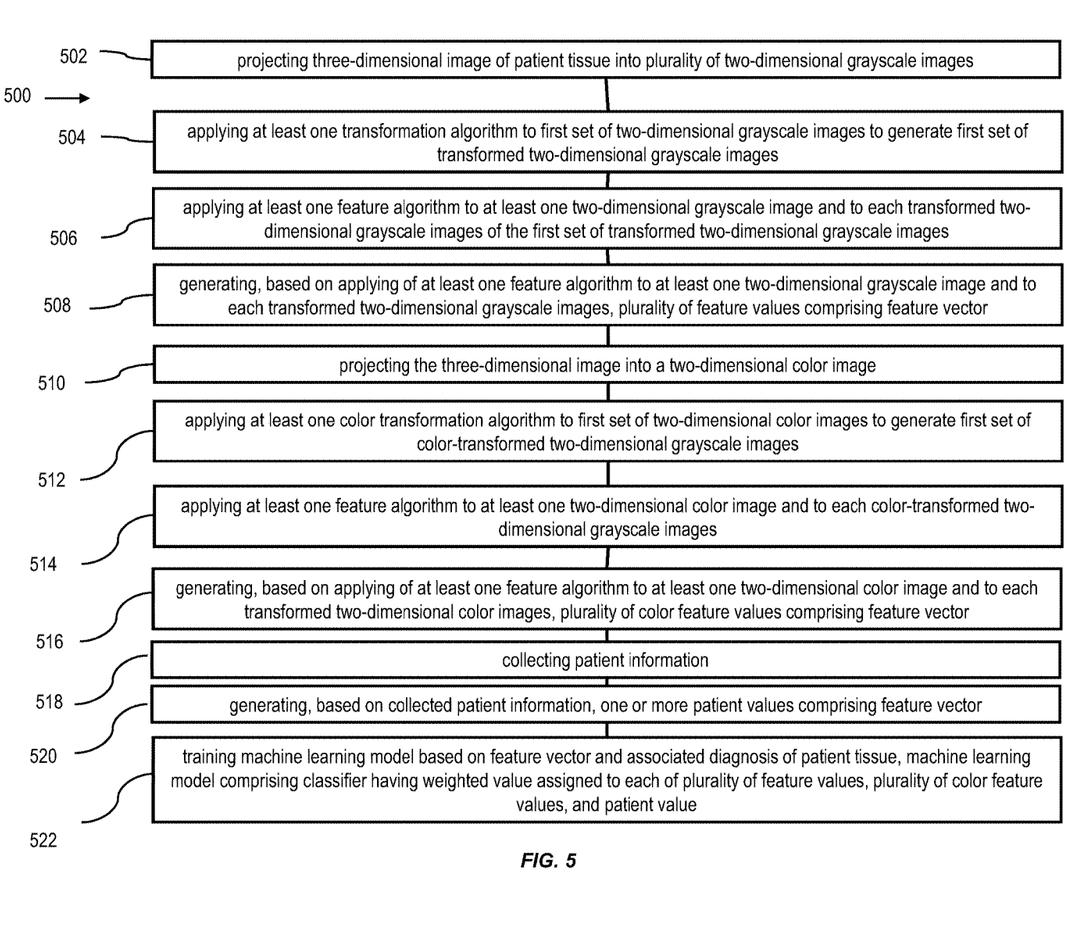
FIG. 5 shows a first process flow diagram illustrating aspects of a method having one or more features consistent with implementations of the current subject matter.

FIG. 5 shows a first process flow chart 500 illustrating features of a method consistent with one or more implementations of the current subject matter. It will be understood that other implementations may include or exclude certain features. At 502, a three-dimensional image of a patient tissue can be projected into a plurality of two-dimensional grayscale images. At 504, at least one transformation algorithm can be applied to a first set of two-dimensional grayscale images to generate a first set of transformed two-dimensional grayscale images. At 506, at least one feature algorithm can be applied to at least one two-dimensional grayscale image and to each transformed two-dimensional grayscale images of the first set of transformed two-dimensional grayscale images. At 508, based on the applying of the at least one feature algorithm to at least one two-dimensional grayscale image and to each transformed two-dimensional grayscale images, a plurality of feature values can be generated that comprise a feature vector. At 510, the three-dimensional image can be projected into a two-dimensional color image. At 512, at least one color transformation algorithm can be applied to a first set of two-dimensional color images to generate a first set of color-transformed two-dimensional grayscale images. At 514, at least one feature algorithm can be applied to at least one two-dimensional color image and to each color-transformed two-dimensional grayscale images. At 516, based on the applying of the at least one feature algorithm to the at least one two-dimensional color image and to each of the transformed two-dimensional color images, a plurality of color feature values can be generated that comprise the feature vector. At 518, patient information can be collected and, at 520, based on the collected patient information, one or more patient values can be generated that comprise the feature vector. At 522, a machine learning model can be trained based on the feature vector and an associated diagnosis of the patient tissue. The machine learning model can include a classifier having a weighted value assigned to each of the plurality of feature values, the plurality of color feature values, and the patient value. In some implementations, the training of the machine learning model can include determining the weighted values by one or more feature ranking algorithms that rank features by their ability to discriminate between classes.

Figure 6:
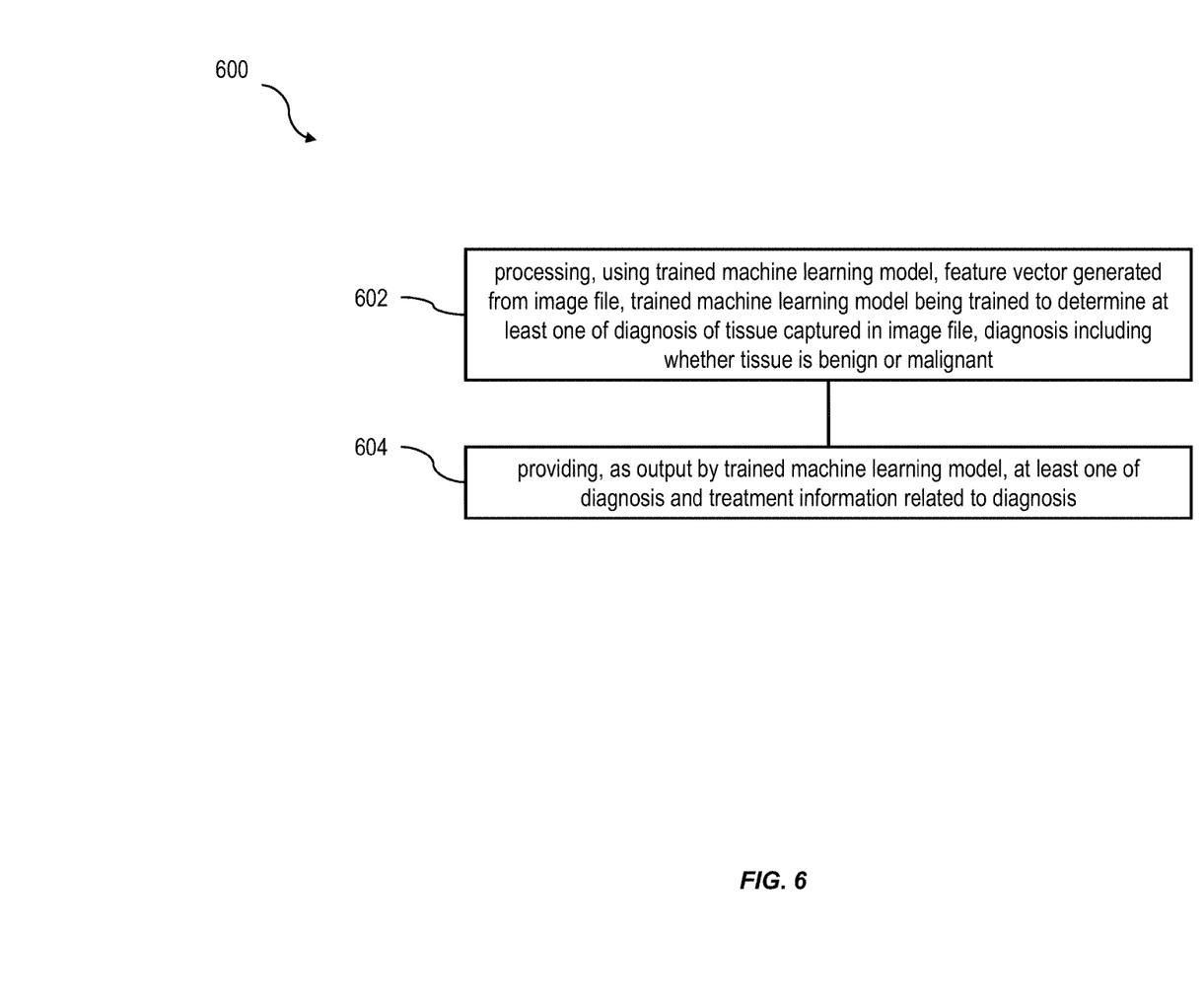
FIG. 6 shows a second process flow diagram illustrating aspects of another method having one or more features consistent with implementations of the current subject matter.

FIG. 6 shows a second process flow chart 600 illustrating features of another method consistent with one or more implementations of the current subject matter. It will be understood that other implementations may include or exclude certain features. At 602, a feature vector can be generated from an image file by processing the feature vector using a trained machine learning model. The trained machine learning model can be trained to determine at least one of a diagnosis of tissue captured in an image file. The diagnosis can include whether the tissue is benign or malignant. At 604, the trained machine learning model can provide an output of at least one of the diagnosis and a treatment information related to the diagnosis.

Figure 7:
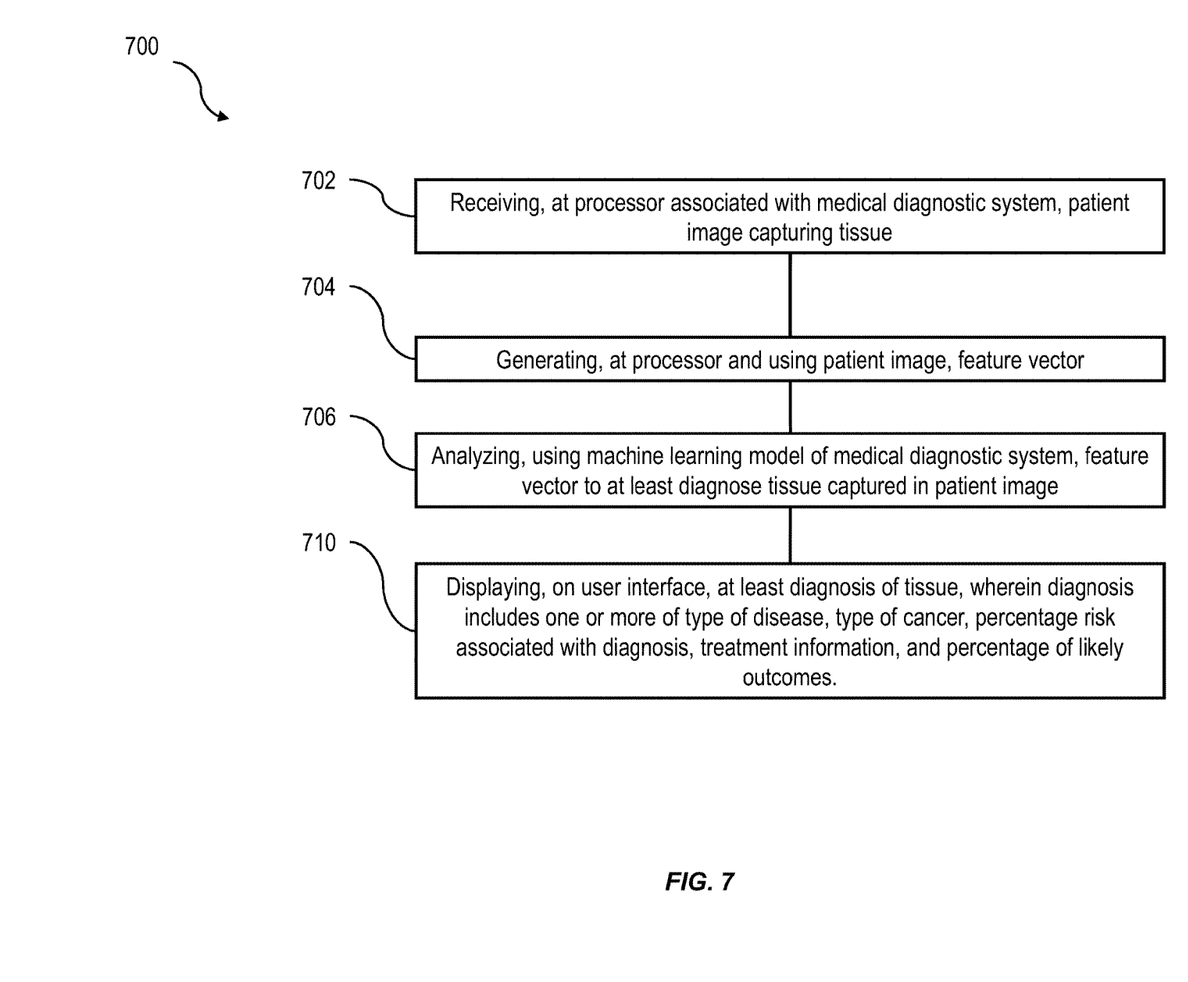
FIG. 7 shows a third process flow diagram illustrating aspects of yet another method having one or more features consistent with implementations of the current subject matter.

FIG. 7 shows a third process flow chart 700 illustrating features of yet another method consistent with one or more implementations of the current subject matter. It will be understood that other implementations may include or exclude certain features. At 702, an image 212 capturing tissue of a patient can be received at processor (e.g., of processing system 102) associated with the medical analytics system 100. At 704, a feature vector 210 can be generated at the processor using at least the image 212 (or part of the image). At 706, the feature vector 210 can be analyzed using the machine learning model 104 of the medical analytics system 100 to at least diagnose the tissue captured in the image 212. At 710, at least the diagnosis of the tissue can be displayed by the user interface 106 of the medical analytics system 100. For example, the diagnosis can include one or more of a type of disease, a type of cancer, a percentage risk associated with diagnosis, a treatment information, and a percentage of likely outcomes.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A system, comprising:
   at least one processor; and
   at least one memory including program code which when executed by the at least one processor provides operations comprising:
   projecting a three-dimensional image of a patient tissue into a plurality of two-dimensional grayscale images;
   applying at least one transformation algorithm to a first set of two-dimensional grayscale images to generate a first set of transformed two-dimensional grayscale images;
   applying at least one feature algorithm to at least one two-dimensional grayscale image and to each transformed two-dimensional grayscale images of the first set of transformed two-dimensional grayscale images;
   generating, based on the applying of the at least one feature algorithm to at least one two-dimensional grayscale image and to each transformed two-dimensional grayscale images, a plurality of feature values comprising a feature vector;
   projecting the three-dimensional image into a two-dimensional color image;
   applying at least one color transformation algorithm to a first set of two-dimensional color images to generate a first set of color-transformed two-dimensional grayscale images;
   applying at least one feature algorithm to at least one two-dimensional color image and to each color-transformed two-dimensional grayscale images;
   generating, based on the applying of the at least one feature algorithm to the at least one two-dimensional color image and to each of the transformed two-dimensional color images, a plurality of color feature values comprising the feature vector;
   collecting patient information;
   generating, based on the collected patient information, one or more patient values comprising the feature vector;
   training a machine learning model based on the feature vector and an associated diagnosis of the patient tissue, the machine learning model comprising a classifier having a weighted value assigned to each of the plurality of feature values, the plurality of color feature values, and the patient value.

2. The system of claim 1, further comprising:
defining, based on the training, a bio-marker that identifies one or more of the color value, the patient value, and at least one of the plurality of feature values, the bio-marker being part of the trained classifier for determining a diagnosis of an undiagnosed tissue captured in an undiagnosed three-dimensional image.

3. The system of claim 2, wherein the diagnosis includes whether the undiagnosed tissue is malignant or benign.

4. The system of claim 2, wherein the undiagnosed tissue is lung tissue or breast tissue.

5. The system of claim 1, wherein the three-dimensional image includes a part of a captured three-dimensional image generated by a three-dimensional imaging system.

6. The system of claim 1, wherein the three-dimensional image is projected onto at least two different dimensional planes thereby generating at least two different two-dimensional grayscale images.

7. A computer-implemented method, comprising:
projecting a three-dimensional image of a patient tissue into a plurality of two-dimensional grayscale images;
applying at least one transformation algorithm to a first set of two-dimensional grayscale images to generate a first set of transformed two-dimensional grayscale images;
applying at least one feature algorithm to at least one two-dimensional grayscale image and to each transformed two-dimensional grayscale images of the first set of transformed two-dimensional grayscale images;
generating, based on the applying of the at least one feature algorithm to at least one two-dimensional grayscale image and to each transformed two-dimensional grayscale images, a plurality of feature values comprising a feature vector;
projecting the three-dimensional image into a two-dimensional color image;
applying at least one color transformation algorithm to a first set of two-dimensional color images to generate a first set of color-transformed two-dimensional grayscale images;
applying at least one feature algorithm to at least one two-dimensional color image and to each color-transformed two-dimensional grayscale images;
generating, based on the applying of the at least one feature algorithm to the at least one two-dimensional color image and to each of the transformed two-dimensional color images, a plurality of color feature values comprising the feature vector;
collecting patient information;
generating, based on the collected patient information, one or more patient values comprising the feature vector;
training a machine learning model based on the feature vector and an associated diagnosis of the patient tissue, the machine learning model comprising a classifier having a weighted value assigned to each of the plurality of feature values, the plurality of color feature values, and the patient value.

8. The computer-implemented method of claim 7, further comprising:
defining, based on the training, a bio-marker that identifies one or more of the color value, the patient value, and at least one of the plurality of feature values, the bio-marker being part of the trained classifier for determining a diagnosis of an undiagnosed tissue captured in an undiagnosed three-dimensional image.

9. The computer-implemented method of claim 8, wherein the diagnosis includes whether the undiagnosed tissue is malignant or benign.

10. The computer-implemented method of claim 8, wherein the undiagnosed tissue is lung tissue or breast tissue.

11. The computer-implemented method of claim 7, wherein the three-dimensional image includes a part of a captured three-dimensional image generated by a three-dimensional imaging system.

12. The computer-implemented method of claim 7, wherein the three-dimensional image is projected onto at least two different dimensional planes thereby generating at least two different two-dimensional grayscale images.

13. A non-transitory computer-readable storage medium including program code which when executed by at least one processor causes operations comprising:
projecting a three-dimensional image of a patient tissue into a plurality of two-dimensional grayscale images;
applying at least one transformation algorithm to a first set of two-dimensional grayscale images to generate a first set of transformed two-dimensional grayscale images;
applying at least one feature algorithm to at least one two-dimensional grayscale image and to each transformed two-dimensional grayscale images of the first set of transformed two-dimensional grayscale images;
generating, based on the applying of the at least one feature algorithm to at least one two-dimensional grayscale image and to each transformed two-dimensional grayscale images, a plurality of feature values comprising a feature vector;
projecting the three-dimensional image into a two-dimensional color image;
applying at least one color transformation algorithm to a first set of two-dimensional color images to generate a first set of color-transformed two-dimensional grayscale images;
applying at least one feature algorithm to at least one two-dimensional color image and to each color-transformed two-dimensional grayscale images;
generating, based on the applying of the at least one feature algorithm to the at least one two-dimensional color image and to each of the transformed two-dimensional color images, a plurality of color feature values comprising the feature vector;
collecting patient information;
generating, based on the collected patient information, one or more patient values comprising the feature vector;
training a machine learning model based on the feature vector and an associated diagnosis of the patient tissue, the machine learning model comprising a classifier having a weighted value assigned to each of the plurality of feature values, the plurality of color feature values, and the patient value.

14. The computer-readable storage medium of claim 13, further comprising:
defining, based on the training, a bio-marker that identifies one or more of the color value, the patient value, and at least one of the plurality of feature values, the bio-marker being part of the trained classifier for determining a diagnosis of an undiagnosed tissue captured in an undiagnosed three-dimensional image.

15. The computer-readable storage medium of claim 14, wherein the diagnosis includes whether the undiagnosed tissue is malignant or benign.

16. The computer-readable storage medium of claim 14, wherein the undiagnosed tissue is lung tissue or breast tissue.

17. The computer-readable storage medium of claim 13, wherein the three-dimensional image includes a part of a captured three-dimensional image generated by a three-dimensional imaging system.

18. The computer-readable storage medium of claim 13, wherein the three-dimensional image is projected onto at least two different dimensional planes thereby generating at least two different two-dimensional grayscale images.

* * * * *